United States Patent
Yokhin et al.

(10) Patent No.: US 6,680,996 B2
(45) Date of Patent: Jan. 20, 2004

(54) DUAL-WAVELENGTH X-RAY REFLECTOMETRY

(75) Inventors: Boris Yokhin, Nazareth Illit (IL); Isaac Mazor, Haifa (IL); Amos Gvirtzman, Moshav Zippori (IL)

(73) Assignee: Jordan Valley Applied Radiation Ltd., Migdal Haemek (IL)

( * ) Notice: Subject to any disclaimer, the term of this patent is extended or adjusted under 35 U.S.C. 154(b) by 129 days.

(21) Appl. No.: 10/078,640

(22) Filed: Feb. 19, 2002

(65) Prior Publication Data

US 2003/0156682 A1 Aug. 21, 2003

(51) Int. Cl.[7] ................................................ G01N 23/20
(52) U.S. Cl. .......................................... 378/70; 378/84
(58) Field of Search ............................ 378/70, 84, 46, 378/89, 90, 73

(56) References Cited

U.S. PATENT DOCUMENTS

| | | | | |
|---|---|---|---|---|
| 5,287,395 A | * | 2/1994 | Khounsary | 378/85 |
| 5,353,324 A | * | 10/1994 | Kitano | 378/73 |
| 5,619,548 A | | 4/1997 | Koppel | 378/70 |
| 5,740,226 A | | 4/1998 | Komiya et al. | 378/70 |
| 5,923,720 A | | 7/1999 | Barton et al. | 378/84 |
| 6,381,303 B1 | | 4/2002 | Vu et al. | 378/46 |
| 6,389,102 B2 | | 5/2002 | Mazor et al. | 378/89 |
| 6,453,006 B1 | * | 9/2002 | Koppel et al. | 378/86 |

OTHER PUBLICATIONS

Wiener, et al., "Characterization of Titanium Nitride Layers by Grazing–Emission X–Ray Fluorescence Spectrometry", Applied Surface Science 125 (1998), pp. 129–136.

* cited by examiner

Primary Examiner—Craig E. Church
Assistant Examiner—Irakli Kiknadze
(74) Attorney, Agent, or Firm—Weingarten, Schurgin, Gagnebin & Lebovici LLP

(57) ABSTRACT

A method for testing a surface includes finding respective first and second critical angles for total external reflection of radiation from an area of the surface at first and second wavelengths. The first and second critical angles are compared to determine an orientation of a tangent to the surface in the area.

34 Claims, 3 Drawing Sheets

DUAL-WAVELENGTH X-RAY REFLECTOMETRY

FIELD OF THE INVENTION

The present invention relates generally to analytical instruments, and specifically to instruments and methods for thin film analysis using X-rays.

BACKGROUND OF THE INVENTION

X-ray reflectometry (XRR) is a well-known technique for measuring the thickness, density and surface quality of thin film layers deposited on a substrate. Such measurements are particularly useful in evaluating layers deposited on semiconductor wafer substrates in the course of integrated circuit manufacture.

X-ray reflectometers are sold by a number of companies, among them Technos (Osaka, Japan), Siemens (Munich, Germany) and Bede Scientific Instrument (Durham, UK). Such reflectometers typically operate by irradiating a sample with a beam of X-rays at grazing incidence, i.e., at a small angle relative to the surface of the sample, near the total external reflection angle of the sample material. Measurement of X-ray intensity reflected from the sample as a function of angle gives a pattern of interference fringes, which is analyzed to determine the properties of the film layers responsible for creating the fringe pattern. The X-ray intensity measurements are commonly made using a detector mounted on a goniometer. More recently, fast X-ray reflectometers have been developed using position-sensitive detectors, such as a proportional counter or an array detector, typically a photodiode array or charge-coupled device (CCD).

For example, U.S. Pat. No. 5,619,548, to Koppel, whose disclosure is incorporated herein by reference, describes an X-ray thickness gauge based on reflectometric measurement. A curved, reflective X-ray monochromator is used to focus X-rays onto the surface of a sample. A position-sensitive detector, such as a photodiode detector array, senses the X-rays reflected from the surface and produces an intensity signal as a function of reflection angle. The angle-dependent signal is analyzed to determine properties of the structure of a thin film layer on the sample, including thickness, density and surface roughness.

U.S. Pat. No. 5,923,720, to Barton et al., whose disclosure is incorporated herein by reference, also describes an X-ray spectrometer based on a curved crystal monochromator. The monochromator has the shape of a tapered logarithmic spiral, which is described as achieving a finer focal spot on a sample surface than prior art monochromators. X-rays reflected or diffracted from the sample surface are received by a position-sensitive detector.

U.S. Pat. No. 5,740,226, to Komiya et al., describes a method for analyzing X-ray reflectometric data to determine film thickness. After measuring X-ray reflectance as a function of angle, an average reflectance curve is fitted to the fringe spectrum. The average curve is based on a formula that expresses attenuation, background and surface roughness of the film. The fitted average reflectance curve is then used in extracting the oscillatory component of the fringe spectrum. This component is Fourier transformed to find the film thickness.

In order to obtain accurate measurements of film thickness, it is necessary to precisely calibrate the angular scale of the reflection. Such a calibration requires, inter alia, exact control of the zero angle of reflection, so that the angle of the reflected beam relative to the surface can be determined accurately. (In the context of the present patent application and in the claims, the term "zero angle" refers to the orientation of a tangent to the reflecting surface at the point of incidence of the radiation.) To make reflectometric measurements with optimal accuracy, the zero angle at the measurement point should be known to within 0.005°.

Although semiconductor wafers appear to be flat, in practice wafers typically deform slightly when held by a vacuum chuck during production or inspection. The deformation is due both to the vacuum force exerted by the chuck and to the weight of the wafer itself. Furthermore, the chuck may have imperfections, such as a slight bend in its axis, that cause deviations in the zero angle of the wafer as it rotates. As a result, inclination of the surface at different sample points on the surface of a wafer may vary by as much as 0.1–0.2°. Therefore, to perform accurate reflectometric measurements at a well-defined measurement point, it becomes necessary to recalibrate the zero angle at each point that is tested on the wafer surface.

SUMMARY OF THE INVENTION

It is an object of some aspects of the present invention to provide improved methods and systems for reflectometry.

It is a further object of some aspects of the present invention to provide methods and devices that enable rapid, accurate determination of the zero angle of a surface under reflectometric inspection.

In preferred embodiments of the present invention, the zero angle of a surface under inspection is calibrated by measuring reflections of X-ray beams from the surface at two different, known wavelengths, $\lambda_1$ and $\lambda_2$. The beams are aligned so as to impinge upon the surface at the same point and along substantially the same direction. Each of the beams generates a reflectometric fringe pattern, which allows the critical angle for total external reflection from the surface to be observed at each of the two wavelengths. Even when the precise zero angle of the surface is not known, the difference between the critical angles at the two different wavelengths can be measured with high precision.

In accordance with known physical principles, the critical angle at X-ray wavelengths is equal to a constant, k, which depends on the density of the reflecting surface layer, multiplied by the wavelength itself. The precise measurement of the difference in the critical angles at the two different measurement wavelengths can thus be used to accurately calculate k with respect to the surface under inspection. Once k is known, the zero angle of the surface at the measurement point is calibrated simply by subtracting $k\lambda$ from the observed critical angle at either of the known wavelengths. The pattern of reflected fringes at either or both of $\lambda_1$ and $\lambda_2$ can then be analyzed to accurately determine local surface properties including thickness, density and roughness of think film layers on the surface.

There is therefore provided, in accordance with a preferred embodiment of the present invention, a method for testing a surface, including:

finding respective first and second critical angles for total external reflection of radiation from an area of the surface at first and second wavelengths; and comparing the first and second critical angles to determine an orientation of a tangent to the surface in the area.

Preferably, comparing the first and second critical angles includes taking an angular difference between the first and second critical angles, and calculating, based on the angular difference, a property of the surface for use in determining the orientation of the tangent. Most preferably, calculating the property includes finding a constant k such that the angular difference between the first and second critical angles is substantially equal to $|k(\lambda_2-\lambda_1)|$, wherein $\lambda_1$ and $\lambda_2$ are the first and second wavelengths, respectively, and setting $k\lambda_1$, equal to the first critical angle so as to find the orientation of the tangent.

Preferably, finding the first and second critical angles includes irradiating the surface with first and second beams of the radiation at the first and second wavelengths, respectively, wherein the first and second beams both impinge on the surface in the area along substantially the same direction. Further preferably, finding the first and second critical angles includes detecting the radiation reflected from the surface using a common detector for the first and second beams. Most preferably, detecting the radiation includes detecting the radiation at the second wavelength while preventing the first beam from impinging on the surface. Alternatively, since the first and second beams have respective first and second photon energies dependent on the first and second wavelengths, detecting the radiation includes discriminating between the radiation detected at the first and second wavelengths responsive to the respective photon energies.

In a preferred embodiment, irradiating the surface includes generating the first and second beams using first and second radiation sources, respectively. Preferably, irradiating the surface includes focusing the first and second beams onto the surface using first and second crystal monochromators, respectively, in mutually-adjacent positions.

In another preferred embodiment, irradiating the surface includes generating the first and second beams using a single radiation source that emits the radiation at the first and second wavelengths. Preferably, irradiating the surface includes focusing the first and second beams onto the surface using a single crystal monochromator for both the first and second wavelengths. Most preferably, the second wavelength is approximately equal to half the first wavelength, so that the crystal monochromator diffracts a first order of the first beam and a second order of the second beam toward the area of the surface. Alternatively, the crystal monochromator includes first and second crystal elements having respective first and second crystal spacings, selected so that the first crystal element diffracts the first beam toward the area of the surface, while the second crystal element diffracts the second beam toward the area of the surface.

Preferably, finding the critical angles includes detecting an oscillatory pattern in the radiation reflected from the area as a function of elevation angle relative to the surface, and the method includes analyzing the pattern, responsive to the orientation of the tangent, so as to determine a property of the surface. In a preferred embodiment, the surface has at least one thin film layer formed thereon, and finding the critical angles includes irradiating the surface with X-rays at the first and second wavelengths, and analyzing the pattern includes analyzing the X-rays reflected from the surface to determine the property of the at least one thin film layer. In a further preferred embodiment, detecting the oscillatory pattern includes observing the oscillatory pattern at both of the first and second wavelengths.

There is also provided, in accordance with a preferred embodiment of the present invention, apparatus for testing a surface, including:

a radiation source, adapted to irradiate an area of the surface at first and second wavelengths;

a detector, adapted to receive radiation reflected from the surface and to generate a signal responsive thereto; and a signal processor, coupled to receive and analyze the signal so as to find respective first and second critical angles for total external reflection of radiation from an area of the surface at the first and second wavelengths, and to compare the first and second critical angles to determine an orientation of a tangent to the surface in the area.

Preferably, the radiation source is adapted to irradiate the surface with first and second beams of the radiation at the first and second wavelengths, respectively, so that the first and second beams both impinge on the surface in the area along substantially the same direction. Further preferably, the detector has a shape and size chosen so as to detect the radiation reflected from the surface in both the first and second beams, substantially without movement of the detector. Most preferably, the radiation source includes a filter, which is operable to prevent the first beam from impinging on the surface while the detector detects the second beam.

There is additionally provided, in accordance with a preferred embodiment of the present invention, a crystal monochromator, including first and second crystal elements, having respective first and second crystal spacings chosen so that the crystal elements diffract radiation incident thereon at respective first and second wavelengths at a selected Bragg angle, the crystal elements having a curvature chosen so as to focus the radiation at the first and second wavelengths to a common focal area.

Preferably, the first and second crystal elements include first and second crystals having respective front surfaces with the chosen curvature, positioned side by side so that the front surfaces define a common curve. Alternatively, the first crystal element includes a bulk crystal having a front surface with the chosen curvature, and the second crystal element includes a thin layer formed on the front surface of the first crystal element.

There is further provided, in accordance with a preferred embodiment of the present invention, a method for testing a surface, including:

finding respective first and second critical angles for total external reflection of radiation from an area of the surface at first and second wavelengths; and comparing the first and second critical angles to determine a property of the surface.

There is moreover provided, in accordance with a preferred embodiment of the present invention, apparatus for testing a surface, including:

a radiation source, adapted to irradiate an area of the surface at first and second wavelengths;

a detector, adapted to receive radiation reflected from the surface and to generate a signal responsive thereto; and a signal processor, coupled to receive and analyze the signal so as to find respective first and second critical angles for total external reflection of radiation from an area of the surface at the first and second wavelengths, and to compare the first and second critical angles to determine a property of the surface.

The present invention will be more fully understood from the following detailed description of the preferred embodiments thereof, taken together with the drawings in which:

DETAILED DESCRIPTION OF PREFERRED EMBODIMENTS

Figure 1:
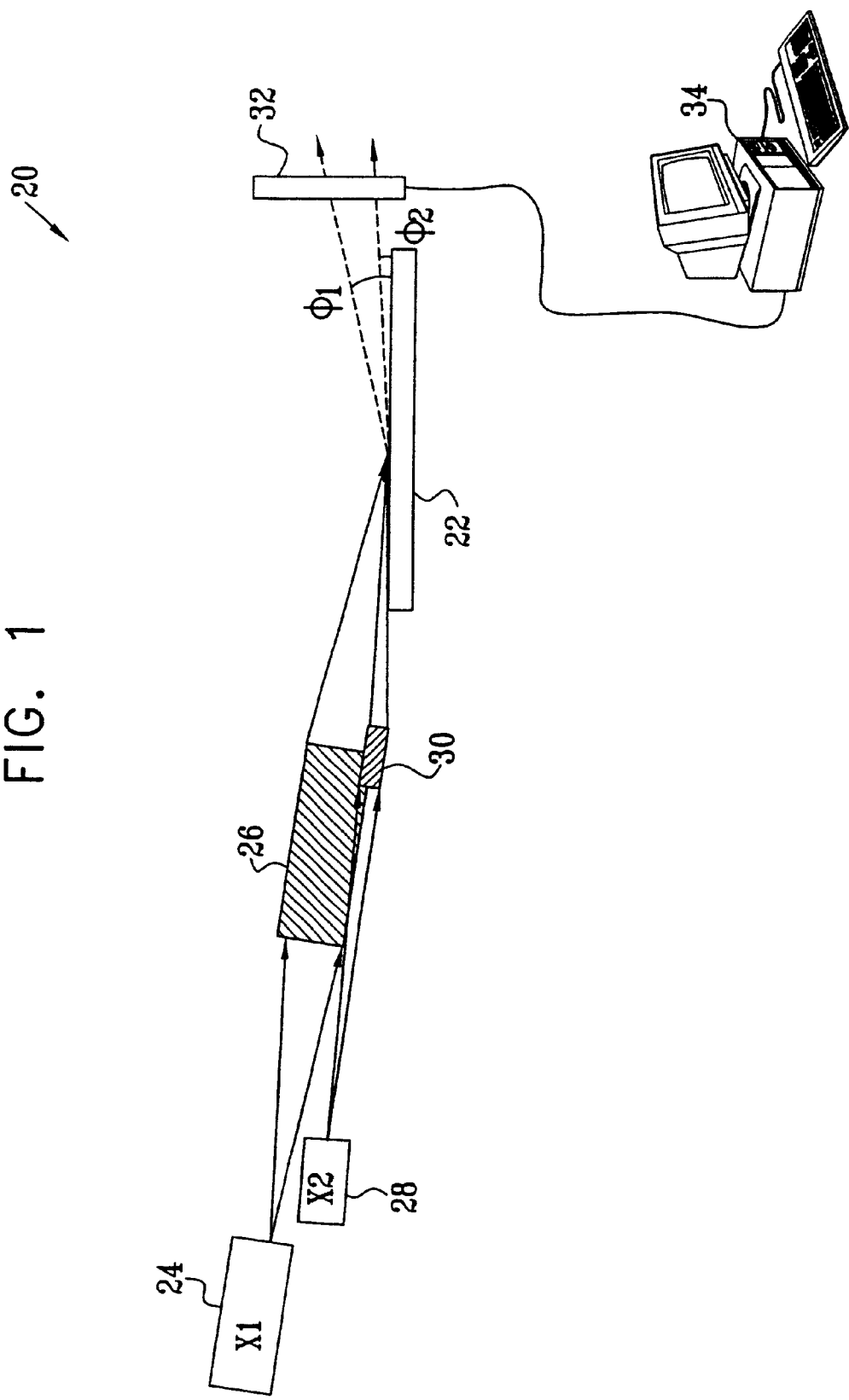
FIG. 1 is a schematic side view of a dual-wavelength system for ref lectometry, in accordance with a preferred embodiment of the present invention.
Figure 2:
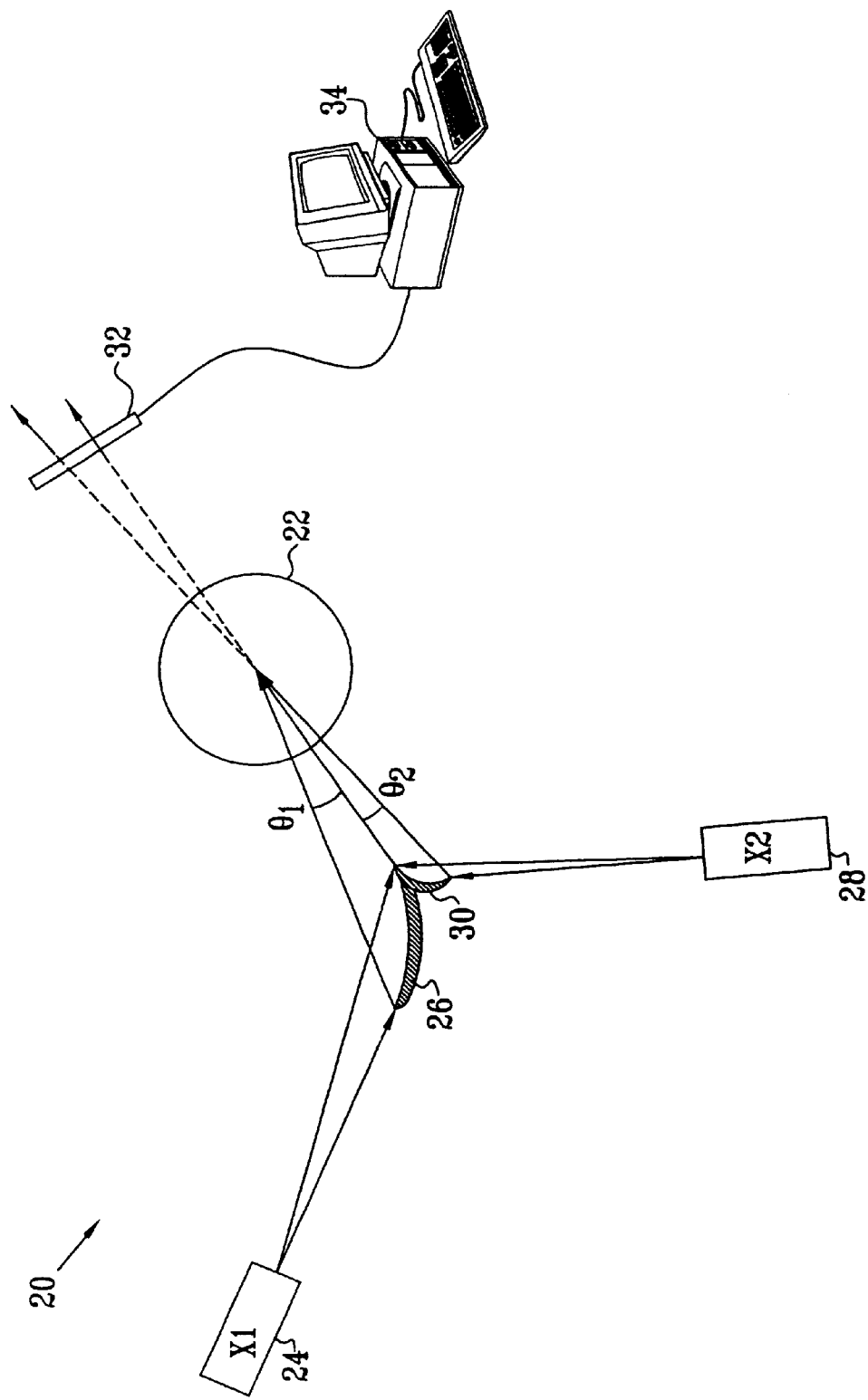
FIG. 2 is a schematic top view of the system of FIG. 1.

Reference is now made to FIGS. 1 and 2, which schematically illustrate a system 20 for X-ray reflectometry of a sample 22, in accordance with a preferred embodiment of the present invention. FIG. 1 shows a side view of the system, while FIG. 2 shows a top view. A first X-ray source 24, typically an X-ray tube, emits a beam of X-rays at a first wavelength $\lambda_1$, which is focused by a first crystal monochromator 26 to irradiate a small area on sample 22. A second X-ray source 28, at another wavelength $\lambda_2$, is focused by a second monochromator 30 to irradiate the same area. Any suitable X-ray tubes may be used for this purpose, such as the XTF5011 tube, produced by Oxford Instruments of Scotts Valley, Cali. To generate the different wavelengths, the tubes used for sources 24 and 28 typically have different anode materials. For example, source 24 may have a copper anode and emit on the CuKa line (8.05 keV), while source 28 has a silver anode emitting on the AuLb line (11.44 keV). Alternative combinations of wavelengths will be apparent to those skilled in the art.

Monochromators 26 and 30 preferably comprise curved crystal monochromators, such as the Doubly-Bent Focusing Crystal Optic, produced by XOS Inc., of Albany, N.Y. Other suitable optics are described in the above-mentioned U.S. Pat. Nos. 5,619,548 and 5,923,720, as well as in U.S. patent application Ser. No. 09/408,894, which is assigned to the assignee of the present patent application and whose disclosure is incorporated herein by reference. Although curved crystal monochromators are particularly convenient for implementing the present invention, other types and configurations of X-ray focusing and monochromatizing optics may also be used, as will be apparent to those skilled in the art.

The X-rays reflected from sample 22 are received by a detector 32. Preferably, detector 32 collects the reflected X-rays over a range of reflection angles between about 0° and 3°, both below and above the critical angle of the sample for total external reflection at both wavelengths $\lambda_1$ and $\lambda_2$. Detector 32 preferably comprises a detector array, such as a CCD array, as is known in the art. Details of the use of CCD arrays in X-ray reflectometry are described in U.S. patent applications Ser. Nos. 09/409,046 and 09/833,902, which are assigned to the assignee of the present patent application, and whose disclosures are incorporated herein by reference.

A signal processor 34 analyzes the output of detector 32, so as to determine a distribution of the flux of X-ray photons reflected from sample 22 as a function of elevation angle $\phi$ at a given energy or over a range of energies. Processor 34 typically comprises a general-purpose computer with suitable input circuits for receiving the detector output, and software for analyzing the reflected radiation intensity, as described in the above-mentioned U.S. patent application Ser. No. 09/833,902. Typically, sample 22 has one or more thin surface layers, such as thin films, so that the distribution of intensity as a function of elevation angle exhibits an oscillatory structure, due to interference effects among reflected X-ray waves from the interfaces between the layers.

Processor 34 analyzes the oscillatory structure of the reflected intensity in order to determine the critical angle for total external reflection from the surface of sample 22 at each of the wavelengths $\lambda_1$ and $\lambda_2$. The oscillatory structure typically has a well-defined shoulder, corresponding to the critical angle, below which the reflectance of the surface is nearly 100%. By finding the shoulder at both wavelengths, processor 34 identifies the critical angles, $\phi_{crit}(\lambda_1)$ and $\phi_{crit}(\lambda_2)$. These are relative values of the critical angles the zero angle at the measurement point on sample 22 is not yet precisely known.

It is well known in the X-ray art that for any wavelength $\lambda$, the critical angle is given by $\phi_{crit}=k\lambda$, wherein k is a wavelength-independent constant (which depends on the square root of the density of the reflecting surface). Therefore, the difference between the relative critical angles at the two measurement wavelengths is also proportional to k, i.e., $\alpha\phi=\phi_{crit}(\lambda_2)-\phi_{crit}(\lambda_1)=k(\lambda_2-\lambda_1)$. Processor 34 can thus compute k precisely based on the known difference between the irradiation wavelengths and the measured difference between the relative critical angles at the two wavelengths. It then uses this value of k to find the absolute value of $\phi_{crit}(\lambda_1)=k\lambda_1$. By subtracting the absolute value from the measured relative value of the critical angle, processor 34 is able to reconstruct the zero angle position exactly. Once the zero angle is known, the processor analyzes the oscillatory structure of the reflections at $\lambda_1$ (and optionally at $\lambda_2$, as well) to determine properties of one or more of the surface layers of sample 22, preferably including thickness, density and surface quality.

In order for the measurement of $\Delta\phi$ to yield an accurate value of k, the X-ray beams at wavelengths $\lambda_1$ and $\lambda_2$ should impinge on substantially the same point on sample 22 along substantially the same direction, without movement of the sample between the measurements at the different wavelengths. For this reason, X-ray sources 24 and 28 and monochromators 26 and 30 are preferably aligned, as shown in the figures, so that the X-ray beams at wavelengths $\lambda_1$ and $\lambda_2$ are as nearly as possible collinear. Assuming that source 24 is the primary source, which is used for subsequent reflectometric analysis of sample 22 (as described above), monochromator 26 should have an effective aperture large enough to give a substantial signal at detector 32 over the full range of elevation angles of interest. The inventors have found that a monochromator with an azimuthal spread $\theta_1$ of 0.85° is typically sufficient for this purpose, with a range of elevations $\phi_1$ from 0° to about 4.50°. (The angles are enlarged in the figures for clarity of illustration.) On the other hand, if source 28 is used only to find the critical angle at wavelength $\lambda_2$, there is no need to collect weak, high-angle reflection signals at $\lambda_2$. Lower collection efficiency is therefore acceptable at this wavelength. It is therefore sufficient for monochromator 30 to have a smaller aperture, typically with $\theta_2=0.25°$, with $\phi_2$ ranging from 0° to about 0.60°.

Alternatively, the short-wavelength beam from source 28 may be used, as well, for measurements over a larger range of elevations. In this case, an oscillatory structure will also be observed in the reflections measured at $\lambda_2$. The short-wavelength oscillations are useful in analyzing the properties of very thin films on sample 22, which may be too thin to be detected effectively at $\lambda_1$.

In the configuration shown in FIGS. 1 and 2, the beams at both $\lambda_1$ and $\lambda_2$ reflect from sample 22 and strike detector 32 side by side. Preferably, assuming detector 32 to comprise a linear array of detector elements, with the array axis running vertically (in the view of FIG. 1), the array elements are wide enough horizontally to capture both beams. In this case, sources 24 and 28 are preferably operated in close alternation, and the critical angle is measured at each of the two wavelengths in succession. Typically, if the signal at $\lambda_2$ is used only to determine the critical angle $\phi_{crit}(\lambda_2)$, source 28 can operate for only a short time, relative to source 24.

Alternatively, if the X-ray photon flux at detector 32 is low, the sources 24 and 28 may be operated simultaneously. In this case, the detector signals at the two wavelengths are preferably distinguished using methods of energy discrimination known in the art. Because the X-ray photons at wavelength $\lambda_2$ are, in the present embodiment, substantially more energetic than the photons at $\lambda_1$, each photon incident on detector 32 at $\lambda_2$ will generate many more secondary electrons in the detector, resulting in a larger output pulse to processor 34. By distinguishing between the pulse heights, the processor can separate the simultaneous signals at the two wavelengths.

Further alternatively, detector 32 may comprise a two-dimensional matrix array of detector elements. In this case, the column or columns of detector elements at the left side of detector 32 (in the view of FIG. 2) will detect the reflected X-rays at $\lambda_2$, while those at the right side will detect the reflected X-rays at $\lambda_1$. In this case, too, sources 24 and 28 can operate simultaneously.

Figure 3:
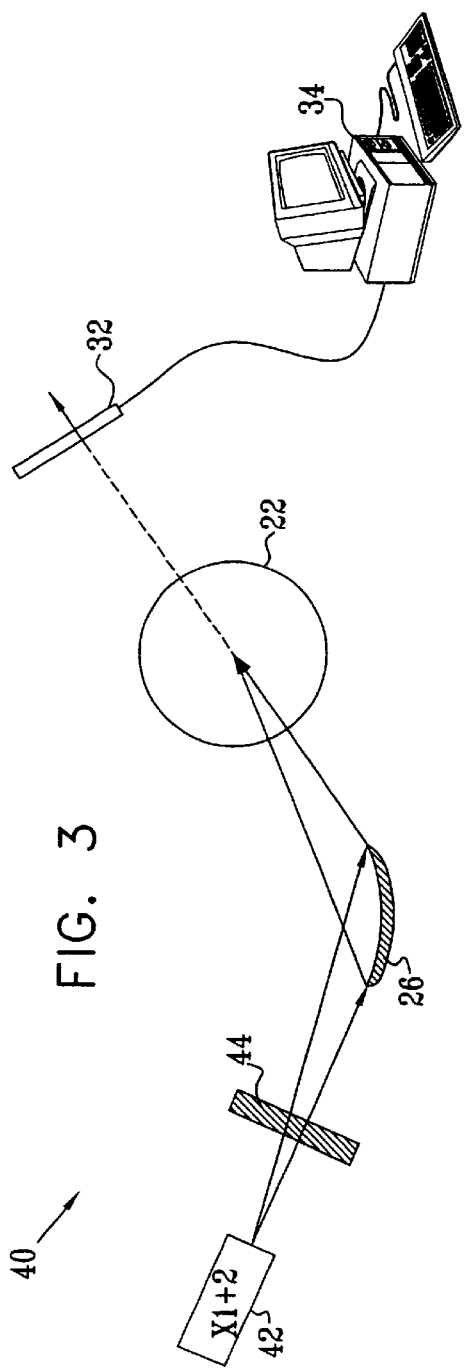
FIG. 3 is a schematic top view of a dual-wavelength system for reflectometry, in accordance with a preferred embodiment of the present invention.

FIG. 3 is a schematic top view of a system 40 for X-ray reflectometry, in accordance with another preferred embodiment of the present invention. This embodiment uses a single X-ray source 42 with two different emission wavelengths. Preferably, the emission wavelengths $\lambda_1$ and $\lambda_2$ are chosen so that $\lambda_1 \cong 2\lambda_2$. Diffraction by crystal monochromator 26 is governed by the Bragg formula, i.e., 2d sin θ=nλ, wherein d is the crystal period, and n is the order of diffraction. When $\lambda_1 = 2\lambda_2$, monochromator 26 reflects and focuses $\lambda_1$ in its first order of diffraction at the same angle as it reflects and focuses $\lambda_2$ in its second order. This arrangement is advantageous in that the two X-ray beams that are used to irradiate sample 22 at $\lambda_1$ and $\lambda_2$ are inherently aligned, and the need for a second monochromator is eliminated.

To implement the embodiment of FIG. 3, for example, source 42 may comprise an X-ray tube having an anode made of copper and strontium, preferably in proportions 80:20 Cu:Sr. The SrKb2 line, at 16.083 keV, is almost exactly half the wavelength of the CuKa1 line, at 8.047 keV. (In energy terms, half the photon energy for SrKb2 is equal to only 5 eV less than the photon energy of CuKa1.) Given this small difference, monochromator 26 will focus both wavelengths efficiently onto the sample, while filtering out all other Cu and Sr wavelengths, with only an insignificant angular deviation between the beams in the azimuthal (θ) direction. The SrKb2 line, which is roughly 30 times weaker than CuKa1, is preferably used only for finding the critical angle $\phi_{crit}(\lambda_2)$. Alternatively, as noted above, the shorter-wavelength radiation may also be used in observing an oscillatory pattern due to a very thin layer on the surface of sample 22.

As another example, the anode of the X-ray tube may comprise chromium and bismuth. The photon energy of the CrKa1 line, at 5.414 keV, is equal to only 4 eV less than half the photon energy of the BiLa1 line, at 10.836 keV. Those skilled in the art will be able to find other suitable line pairs, as well.

A filter 44, typically comprising a thick layer of aluminum, is preferably used to block the CuKa1 radiation while making the measurement at SrKb2. (Optionally, the SrKb2 radiation may similarly be blocked while the CuKa1 radiation is measured.) Alternatively, the measurements at both wavelengths may be made simultaneously, using energy discrimination to separate the signals, as described above.

Alternatively, dual-wavelength source 42 may be configured to emit X-rays at two different wavelengths that are not multiples of one another, as long as the X-ray optics used to focus and monochromatize the radiation incident on sample 22 are capable of handling both wavelengths. Assuming a curved crystal monochromator is used, as described above, this requirement can be met by assembling the monochromator from two different crystals, having respective spacings $d_1$ and $d_2$, selected so that $d_2/d_1 = \lambda_2/\lambda_1$.

Figure 4B:
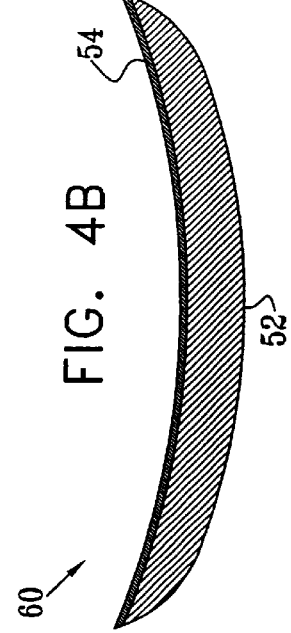
FIGS. 4A and 4B are schematic, sectional views of curved monochromators used in dual-wavelength reflectometry, in accordance with preferred embodiments of the present invention.
Figure 4A:
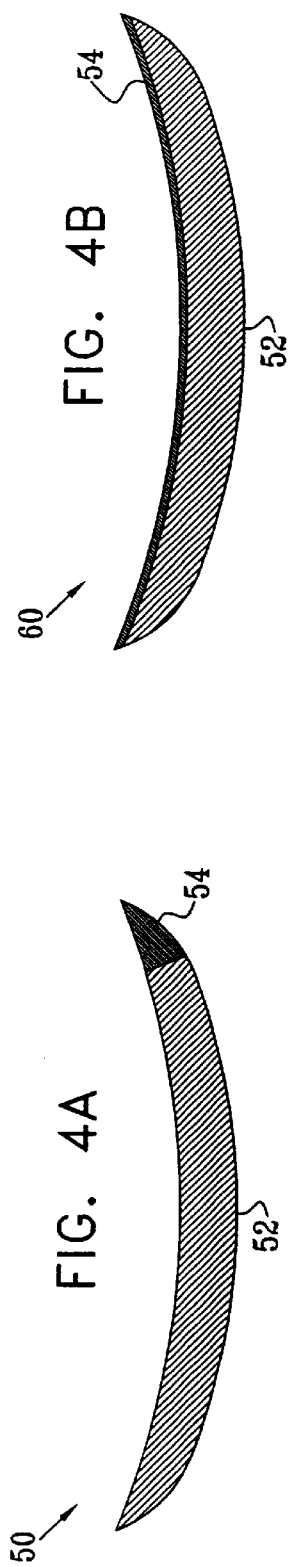

FIG. 4A is a schematic, sectional view of a crystal monochromator 50 designed in this manner for dual-wavelength operation, in accordance with a preferred embodiment of the present invention. A first crystal element 52, with spacing $d_1$ chosen for operation at wavelength $\lambda_1$, makes up approximately 90% of the area of monochromator 50. A second crystal element 54, with spacing $d_2$ for operation at $\lambda_2$, makes up the remainder of the monochromator. As long as the proper ratio of the spacings $d_1$ and $d_2$ is maintained, and crystal element 54 has the same curvature as crystal element 52, the two crystals will have the same focal point for their respective wavelengths.

FIG. 4B is a schematic, sectional view of a crystal monochromator 60 designed for dual-wavelength operation, in accordance with another preferred embodiment of the present invention. In this embodiment, crystal element 54 is formed as a thin layer over crystal element 52, which is a bulk crystal. This arrangement of the crystals is preferably created by growing the layer of crystal element 54 on a substrate of crystal element 52, using methods of thin- or thick-film deposition known in the art.

Although the preferred embodiments described above make reference specifically to X-ray reflectometry, the principles of the present invention may similarly be applied, mutatis mutandis, in other fields of X-ray analysis. For example, the methods of the preferred embodiment may be used to find the zero-angle in X-ray diffractometry, as well as X-ray fluorescence (XRF) analysis, including particularly grazing emission XRF. Grazing emission XRF is described, for example, in an article by Wiener et al., entitled "Characterization of Titanium Nitride Layers by Grazing-Emission X-ray Fluorescence Spectrometry," in Applied Surface *Science* 125 (1998), p. 129, which is incorporated herein by reference. The principles of the present invention may also be implemented in angle-sensitive detection systems for other energy ranges, such as for detection of gamma rays and other nuclear radiation.

It will thus be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A method for testing a surface, comprising:

finding respective first and second critical angles for total external reflection of radiation from an area of the surface at first and second wavelengths; and comparing the first and second critical angles to determine an orientation of a tangent to the surface in the area.

2. A method according to claim 1, wherein comparing the first and second critical angles comprises taking an angular difference between the first and second critical angles, and calculating, based on the angular difference, a property of the surface for use in determining the orientation of the tangent.

3. A method according to claim 2, wherein calculating the property comprises finding a constant k such that the angular difference between the first and second critical angles is substantially equal to $|k(\lambda_2-\lambda_1)|$, wherein $\lambda_1$ and $\lambda_2$ are the first and second wavelengths, respectively, and setting $k\lambda_1$ equal to the first critical angle so as to find the orientation of the tangent.

4. A method according to claim 1, wherein finding the first and second critical angles comprises irradiating the surface with first and second beams of the radiation at the first and second wavelengths, respectively, wherein the first and second beams both impinge on the surface in the area along substantially the same direction.

5. A method according to claim 4, wherein finding the first and second critical angles comprises detecting the radiation reflected from the surface using a common detector for the first and second beams.

6. A method according to claim 5, wherein detecting the radiation comprises detecting the radiation at the second wavelength while preventing the first beam from impinging on the surface.

7. A method according to claim 5, wherein the first and second beams have respective first and second photon energies dependent on the first and second wavelengths, and wherein detecting the radiation comprises discriminating between the radiation detected at the first and second wavelengths responsive to the respective photon energies.

8. A method according to claim 4, wherein irradiating the surface comprises generating the first and second beams using first and second radiation sources, respectively.

9. A method according to claim 8, wherein irradiating the surface comprises focusing the first and second beams onto the surface using first and second crystal monochromators, respectively, in mutually-adjacent positions.

10. A method according to claim 4, wherein irradiating the surface comprises generating the first and second beams using a single radiation source that emits the radiation at the first and second wavelengths.

11. A method according to claim 10, wherein irradiating the surface comprises focusing the first and second beams onto the surface using a single crystal monochromator for both the first and second wavelengths.

12. A method according to claim 11, wherein the second wavelength is approximately equal to half the first wavelength, so that the crystal monochromator diffracts a first order of the first beam and a second order of the second beam toward the area of the surface.

13. A method according to claim 11, wherein the crystal monochromator comprises first and second crystal elements having respective first and second crystal spacings, selected so that the first crystal element diffracts the first beam toward the area of the surface, while the second crystal element diffracts the second beam toward the area of the surface.

14. A method according to claim 1, wherein finding the critical angles comprises detecting an oscillatory pattern in the radiation reflected from the area as a function of elevation angle relative to the surface, and comprising analyzing the pattern, responsive to the orientation of the tangent, so as to determine a property of the surface.

15. A method according to claim 14, wherein the surface has at least one thin film layer formed thereon, and wherein finding the critical angles comprises irradiating the surface with X-rays at the first and second wavelengths, and wherein analyzing the pattern comprises analyzing the X-rays reflected from the surface to determine the property of the at least one thin film layer.

16. A method according to claim 14, wherein detecting the oscillatory pattern comprises observing the oscillatory pattern at both of the first and second wavelengths.

17. Apparatus for testing a surface, comprising:
a radiation source, adapted to irradiate an area of the surface at first and second wavelengths;
a detector, adapted to receive radiation reflected from the surface and to generate a signal responsive thereto; and
a signal processor, coupled to receive and analyze the signal so as to find respective first and second critical angles for total external reflection of radiation from an area of the surface at the first and second wavelengths, and to compare the first and second critical angles to determine an orientation of a tangent to the surface in the area.

18. Apparatus according to claim 17, wherein the processor is adapted to determine the orientation of the tangent by taking an angular difference between the first and second critical angles, and calculating, based on the angular difference, a property of the surface for use in determining the orientation of the tangent.

19. Apparatus according to claim 18, wherein the property calculated by the processor comprises a constant k such that the angular difference between the first and second critical angles is substantially equal to $|k(\lambda_2-\lambda_1)|$, wherein $\lambda_1$ and $\lambda_2$ are the first and second wavelengths, respectively, and wherein the processor is adapted to find the orientation of the tangent by setting $k\lambda_1$ equal to the first critical angle.

20. Apparatus according to claim 17, wherein the radiation source is adapted to irradiate the surface with first and second beams of the radiation at the first and second wavelengths, respectively, so that the first and second beams both impinge on the surface in the area along substantially the same direction.

21. Apparatus according to claim 20, wherein the detector has a shape and size chosen so as to detect the radiation reflected from the surface in both the first and second beams, substantially without movement of the detector.

22. Apparatus according to claim 21, wherein the radiation source comprises a filter, which is operable to prevent the first beam from impinging on the surface while the detector detects the second beam.

23. Apparatus according to claim 21, wherein the first and second beams have respective first and second photon energies dependent on the first and second wavelengths, and wherein the signal processor is adapted to distinguish between the radiation detected at the first and second wavelengths responsive to the respective photon energies.

24. Apparatus according to claim 20, wherein the radiation source comprises first and second radiation sources, which are adapted to generate the first and second beams, respectively.

25. Apparatus according to claim 24, wherein the first and second radiation sources comprise respective first and second crystal monochromators, in mutually-adjacent positions, which are adapted to focus the first and second beams.

26. Apparatus according to claim 20, wherein the radiation source comprises a single source, which is adapted to generate both the first and second beams.

27. Apparatus according to claim 26, wherein the radiation source comprises a single crystal monochromator, which is adapted to focus both the first and second beams.

28. Apparatus according to claim 27, wherein the second wavelength is approximately equal to half the first wavelength, so that the crystal monochromator diffracts a first order of the first beam and a second order of the second beam toward the area of the surface.

29. Apparatus according to claim 27, wherein the crystal monochromator comprises first and second crystal elements having respective first and second crystal spacings, selected so that the first crystal element diffracts the first beam toward the area of the surface, while the second crystal element diffracts the second beam toward the area of the surface.

30. Apparatus according to claim 17, wherein the signal processor is adapted to detect an oscillatory pattern in the radiation reflected from the area as a function of elevation angle relative to the surface, and to analyze the pattern, responsive to the orientation of the tangent, so as to determine a property of the surface.

31. Apparatus according to claim 30, wherein the surface has at least one thin film layer formed thereon, and wherein the radiation source comprises an X-ray source, adapted to emit X-rays at the first and second wavelengths, and wherein the signal processor is adapted to analyze the X-rays reflected from the surface to determine the property of the at least one thin film layer.

32. Apparatus according to claim 30, wherein the signal processor is adapted to detect the oscillatory pattern at both of the first and second wavelengths.

33. A method for testing a surface, comprising:

finding respective first and second critical angles for total external reflection of radiation from an area of the surface at first and second wavelengths; and comparing the first and second critical angles to determine a property of the surface.

34. Apparatus for testing a surface, comprising:

a radiation source, adapted to irradiate an area of the surface at first and second wavelengths;

a detector, adapted to receive radiation reflected from the surface and to generate a signal responsive thereto; and a signal processor, coupled to receive and analyze the signal so as to find respective first and second critical angles for total external reflection of radiation from an area of the surface at the first and second wavelengths, and to compare the first and second critical angles to determine a property of the surface.

* * * * *

UNITED STATES PATENT AND TRADEMARK OFFICE
CERTIFICATE OF CORRECTION

PATENT NO. : 6,680,996 B2
DATED : January 20, 2004
INVENTOR(S) : Boris Yokhin et al.

It is certified that error appears in the above-identified patent and that said Letters Patent is hereby corrected as shown below:

Column 4,
Line 65, "ref lectometry" should read -- reflectometry --;

Column 6,
Line 9, "angles the" should read -- angles, since the --; and
Line 18, "$\alpha\phi=\phi_{crit}(\lambda_2) -\phi_{crit}(\lambda_1) =k (\lambda_2-\lambda_1)$" should read -- $\Delta\phi=\phi_{crit}(\lambda_2) -\phi_{crit}(\lambda_1) =k (\lambda_2-\lambda_1)$ --.

Signed and Sealed this

Fourteenth Day of December, 2004

JON W. DUDAS
*Director of the United States Patent and Trademark Office*